US00PP27823P3

(12) United States Plant Patent
Randag

(10) Patent No.: US PP27,823 P3
(45) Date of Patent: Mar. 28, 2017

(54) CALLA LILY PLANT NAMED 'MEMORIES'

(50) Latin Name: *Zantedeschia sprengeri*
Varietal Denomination: Memories

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 58 days.

(21) Appl. No.: 14/544,312

(22) Filed: Dec. 22, 2014

(65) Prior Publication Data

US 2015/0296683 P1 Oct. 15, 2015

Related U.S. Application Data

(60) Provisional application No. 61/964,771, filed on Jan. 14, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV-International Union for the Protection of New Varieties of Plants: PLUTO Plant Variety Database; May 19, 2016; cultivar name—'Memories' (1 pg).*

* cited by examiner

*Primary Examiner* — Susan McCormick Ewoldt
(74) *Attorney, Agent, or Firm* — The Webb Law Firm

(57) ABSTRACT

'Memories' is a new variety of calla lily having inflorescences with a nearly black, dark purple colored spathe that produces 4-16 inflorescences per tuber. The inflorescence stems are about 30 cm in height, and the leaves vary between dark purple and dark green and have whitish spots with a leathery texture.

2 Drawing Sheets

Botanical classification: *Zantedeschia sprengeri*.
Varietal denomination: 'MEMORIES'.

BACKGROUND OF THE NEW PLANT

The present invention comprises a new and distinct cultivar of calla lily, botanically known as *Zantedeschia sprengeri* and hereinafter referred to by the cultivar name 'Memories'.

'Memories' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* seedling referred to as Z020039 (female parent, unpatented) with a *Zantedeschia sprengeri* seedling referred to as Z020015 (male parent, unpatented). 'Memories' was selected in 2007 by the inventor in 't Zand, The Netherlands as one flowering plant within the progeny of the stated cross.

The first act of asexual reproduction of 'Memories' by tissue culture was performed by the inventor in September of 2007 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Memories' which, in combination, distinguish this calla lily as a new and distinct cultivar:

1. Nearly black colored spathe;
2. Dark purple-green colored leaves; and
3. High inflorescence production.

Further, when compared to calla lily plant named 'Black Star' (U.S. Plant Pat. No. 14,844), the upper and lower surface spathe color of 'Black Star' varies between Greyed-Purple Group RHS 187A and Black Group RHS 202A, while the upper and lower surface spathe color of 'Memories' varies between Greyed-Purple Group RHS N186A and N186B.

Table 1 provides similarities and differences of 'Memories' to its parents, *Zantedeschia sprengeri* seedlings Z020039 and Z020015.

TABLE 1

| 'Memories' | Similarities | Differences |
|---|---|---|
| Z020039 | White spots on leaves<br>Plant height | Spathe color (Greyed-Purple Group RHS 187A)<br>Spathe shape (Funnel) |
| Z020015 | Leaf shape<br>Plant height<br>Spathe shape | Leaf color (Between Green Group RHS N134A and 137B)<br>Spathe color (Between Greyed-Purple Group RHS N186A and 187A) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

THE PLANT

Figure 1:
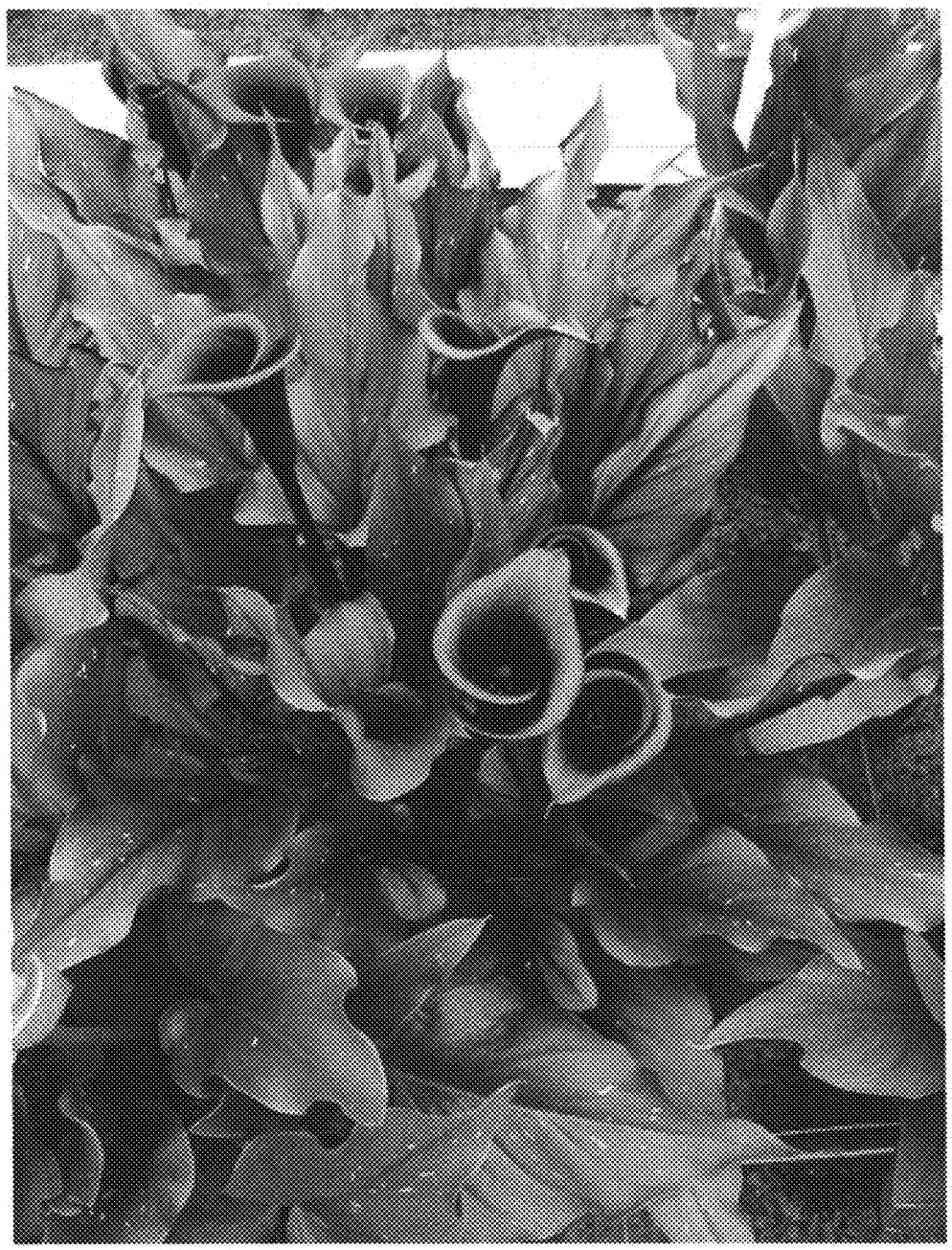
FIG. 1 is a photograph of an overhead view of a plant of the new variety.
Figure 2:
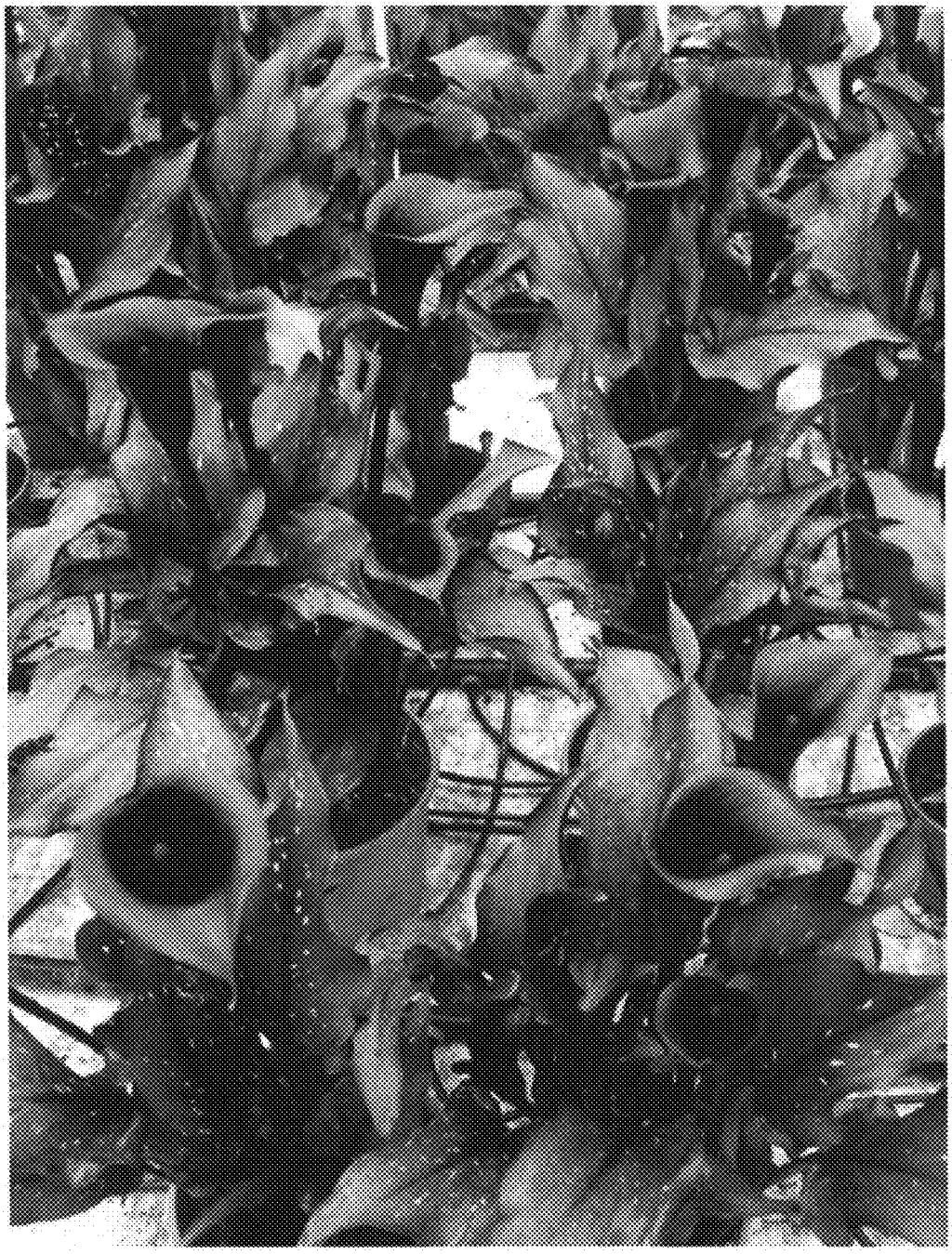
FIG. 2 is a photograph of a group of multiple plants of the new variety.

Size:

*Height of the leaf canopy above the soil.*—10-45 cm.

*Height of top of inflorescence above the soil.*—12-40 cm.

*Diameter.*—18-48 cm.

Form: Erect.

Number of inflorescences per tuber:

*Size* 14-16 cm *in diameter.*—4-6 inflorescences.

*Size* 16-18 cm *in diameter.*—6-11 inflorescences.

*Size* 18-20 cm *in diameter.*—7-16 inflorescences.

Branches:

*Character.*—Many (from 2-6); like the variety 'Odessa' (U.S. Plant Pat. No. 18,833).

*Color.*—Between Greyed-Purple Group RHS N186B and N186C.

Leaves:

*Size.*—Width: 1.5-13 cm. Length: 7-22 cm.

*Number per plant.*—15-40.

*Shape.*—Sagittate.

*Color.*—Upper surface: Green Group RHS 136B to Greyed-Purple Group RHS N186B, with transparent White Group RHS 155A and N155 spots. Lower surface: Green Group RHS 137B to Greyed-Purple Group RHS N186B, with transparent White Group RHS 155A and N155 spots.

*Apex.*—Apiculate.

*Base.*—Truncate.

*Margin.*—Undulate; having a color of Greyed-Purple Group RHS N186B to N186C.

*Veins.*—Configuration: Pinnate. Color: Greyed-Purple Group RHS 186B to N186C.

*Surface quality.*—Leathery.

*Petiole.*—Length: 5-25 cm. Diameter: 8 mm. Color: The base is Red-Purple Group RHS 69A, and the upper part is Greyed-Purple Group RHS N186C to 187A.

Roots:

*Color.*—White.

*Branching.*—Similar to other *Zantedeschia* varieties.

THE INFLORESCENCE AND SEEDS

Spathe:

*Size.*—Length (measured from base opening to tip): 5-8 cm. Width: 3-6.5 cm. Height: 4-8 cm.

*Color.*—Upper surface: Varies between Greyed-Purple Group RHS N186A and N186B. Lower surface: Varies between Greyed-Purple Group RHS N186A and N186B.

*Vein color.*—Between Greyed-Purple Group RHS N186A and N186B.

*Shape.*—Cupped.

*Apex.*—Obtuse.

*Base.*—Rounded.

*Texture.*—Smooth (upper and lower surfaces).

Spadix:

*Size.*—Length: 35-65 mm. Diameter: 3-13 mm.

*Color.*—Between Greyed-Purple Group RHS N186A and N186B.

*Position relative to spathe.*—Upright.

Peduncle:

*Size.*—Length: 7-32 cm. Diameter: 4-13 mm.

*Color.*—The upper part is between Greyed-Purple Group RHS 186A to N186B, and the lower part is Greyed-Purple Group RHS 186B.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Greyed-Purple Group RHS N186A and N186B.

*Filament.*—Length: Less than 1 mm. Color: Between Greyed-Purple Group RHS N186A and N186B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Green Group RHS 138C and 138D.

*Ovaries.*—Texture: Smooth. Length: Between 1 to 10 mm. Width: Between 1 to 10 mm. Color: Top color is between Greyed-Purple Group RHS N186A and N186B, bottom color is from White Group RHS 155B to 157C.

Seeds:

*Length.*—4-7 mm.

*Width.*—3-6 mm.

*Color.*—Between Purple Group RHS N79A and N79D.

*Amount.*—Between 1-60.

Fruit:

*Amount.*—Multiple berries produced.

*Shape.*—Irregular.

*Color*.—Exhibits a main color that varies between Purple Group RHS N79A and N79B and a secondary color of Black Group RHS 202A.

GENERAL

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Memories' as herein described and illustrated.

* * * * *